US009594872B2

(12) United States Patent
Masarie, Jr. et al.

(10) Patent No.: US 9,594,872 B2
(45) Date of Patent: *Mar. 14, 2017

(54) METHOD AND SYSTEM FOR CONCEPT-BASED TERMINOLOGY MANAGEMENT

(71) Applicant: Intelligent Medical Objects, Inc., Northbrook, IL (US)

(72) Inventors: Fred E. Masarie, Jr., Portland, OR (US); Gregory Richard Aldin, Oak Park, IL (US); David Alvin, Glen Ellyn, IL (US); Aziz M. Bodal, Skokie, IL (US); Matthew Charles Cardwell, Oak Park, IL (US); Régis J P Charlot, Lake Bluff, IL (US); Eric Nathan Frank, Chicago, IL (US); Andrew S. Kanter, New York, NY (US); Masayo Kobashi, Long Grove, IL (US); Jose Antonio Maldonado, Jr., Chicago, IL (US); Frank Naeymi-Rad, Libertyville, IL (US); Alina Oganesova, New York, NY (US); Andre L. Young, Jr., Kenosha, WI (US); Amy Yunhsin Wang, Chicago, IL (US)

(73) Assignee: Intelligent Medical Objects, Inc., Northbrook, IL (US)

( * ) Notice: Subject to any disclaimer, the term of this patent is extended or adjusted under 35 U.S.C. 154(b) by 177 days.

This patent is subject to a terminal disclaimer.

(21) Appl. No.: 13/660,512

(22) Filed: Oct. 25, 2012

(65) Prior Publication Data

US 2014/0122117 A1    May 1, 2014

(51) Int. Cl.
*G06Q 50/22* (2012.01)
*G06Q 50/24* (2012.01)
(Continued)

(52) U.S. Cl.
CPC .......... *G06F 19/322* (2013.01); *G06Q 10/10* (2013.01); *G06Q 50/22* (2013.01); *G06Q 50/24* (2013.01)

(58) Field of Classification Search
CPC .. G06F 19/322; G06F 19/345; G06F 17/2785; G06F 17/3053; G06F 17/30011;
(Continued)

(56) References Cited

U.S. PATENT DOCUMENTS 5,799,268 A    8/1998  Boguraev
5,930,788 A    7/1999  Wical
(Continued)

OTHER PUBLICATIONS

"Semantic Web: Asking the Right Questions", Duch et al., Seventh International Conference on Information and Management Sciences, Urumchi, China, Aug. 12-19, 2008 entire document www.fizyka.umk.pl/ftp/pub/papers/kmk/08-SemWeb.pdf.
(Continued)

*Primary Examiner* — Maroun Kanaan
(74) *Attorney, Agent, or Firm* — Beem Patent Law Firm

(57) ABSTRACT

A method for implementing an interface terminology is described, the interface terminology comprising concepts and descriptions, a description being an alternative way to express a concept. The interface terminology also may include a plurality of domains, wherein each concept is unique within a domain. The method may include the steps of: storing a plurality of concepts in a database; storing a plurality of descriptions in a database; linking each description to a respective concept; storing an external code set in a database, the external code set comprising a plurality of external codes; and mapping an external code to a concept. The steps may occur via database table mapping. The method also may include deploying a front-end file, the front-end file comprises a link between the descriptions and the external code set.

29 Claims, 12 Drawing Sheets

(51) Int. Cl.
*G06F 17/30* (2006.01)
*G06F 19/00* (2011.01)
*G06Q 10/10* (2012.01)

(58) Field of Classification Search
CPC ......... G06F 17/30684; G06F 17/30705; G06F 17/30731; G06F 17/20; G06F 17/30; G06F 17/30424; G06F 17/30528; G06Q 50/22; G06Q 50/24; G06Q 10/10
USPC .......................................................... 705/2, 3
See application file for complete search history.

(56) References Cited

U.S. PATENT DOCUMENTS

| | | | |
|---|---|---|---|
| 6,055,540 A | | 4/2000 | Snow |
| 6,101,515 A | | 8/2000 | Wical et al. |
| 6,904,432 B2 | | 6/2005 | Charlot et al. |
| 7,167,858 B2 | | 1/2007 | Naeymi-Rad et al. |
| 7,496,593 B2 | | 2/2009 | Gardner et al. |
| 7,536,387 B2 | | 5/2009 | Charlot et al. |
| 7,610,192 B1 * | 10/2009 | Jamieson .......................... 704/9 |
| 7,693,917 B2 | | 4/2010 | Charlot et al. |
| 7,711,671 B2 | | 5/2010 | Meyers |
| 7,870,117 B1 | | 1/2011 | Rennison |
| 8,346,804 B2 * | 1/2013 | Phillips .......................... 707/780 |
| 2005/0240572 A1 | 10/2005 | Sung et al. |
| 2007/0179776 A1 | 8/2007 | Segond et al. |
| 2008/0065452 A1 | 3/2008 | Naeymi-Rad et al. |
| 2008/0306926 A1 | 12/2008 | Friedlander et al. |
| 2009/0083231 A1 | 3/2009 | Eberholst et al. |
| 2009/0254572 A1 | 10/2009 | Redlich et al. |
| 2010/0169299 A1 | 7/2010 | Pollara |
| 2010/0262659 A1 | 10/2010 | Christiansen et al. |
| 2011/0066425 A1 | 3/2011 | Hudgins et al. |
| 2011/0138050 A1 | 6/2011 | Dawson et al. |
| 2011/0184960 A1 | 7/2011 | Delpha et al. |
| 2012/0179696 A1 | 7/2012 | Charlot et al. |

OTHER PUBLICATIONS

"Social tagging overview (SharePoint Server 2010)" May 12, 2010 entire document http://technet.microsoft.com/en-us/library/ff608137.aspx.

Bronnert, et al., Problem-Centered Care Delivery, Journal of AHIMA 83, No. 7 (Jul. 2012): 30-35.

Notification of Transmittal of the International Search Report and Written Opinion dated Feb. 26, 2014, issued in International Application No. PCT/US2013/066305 (18 pages).

* cited by examiner

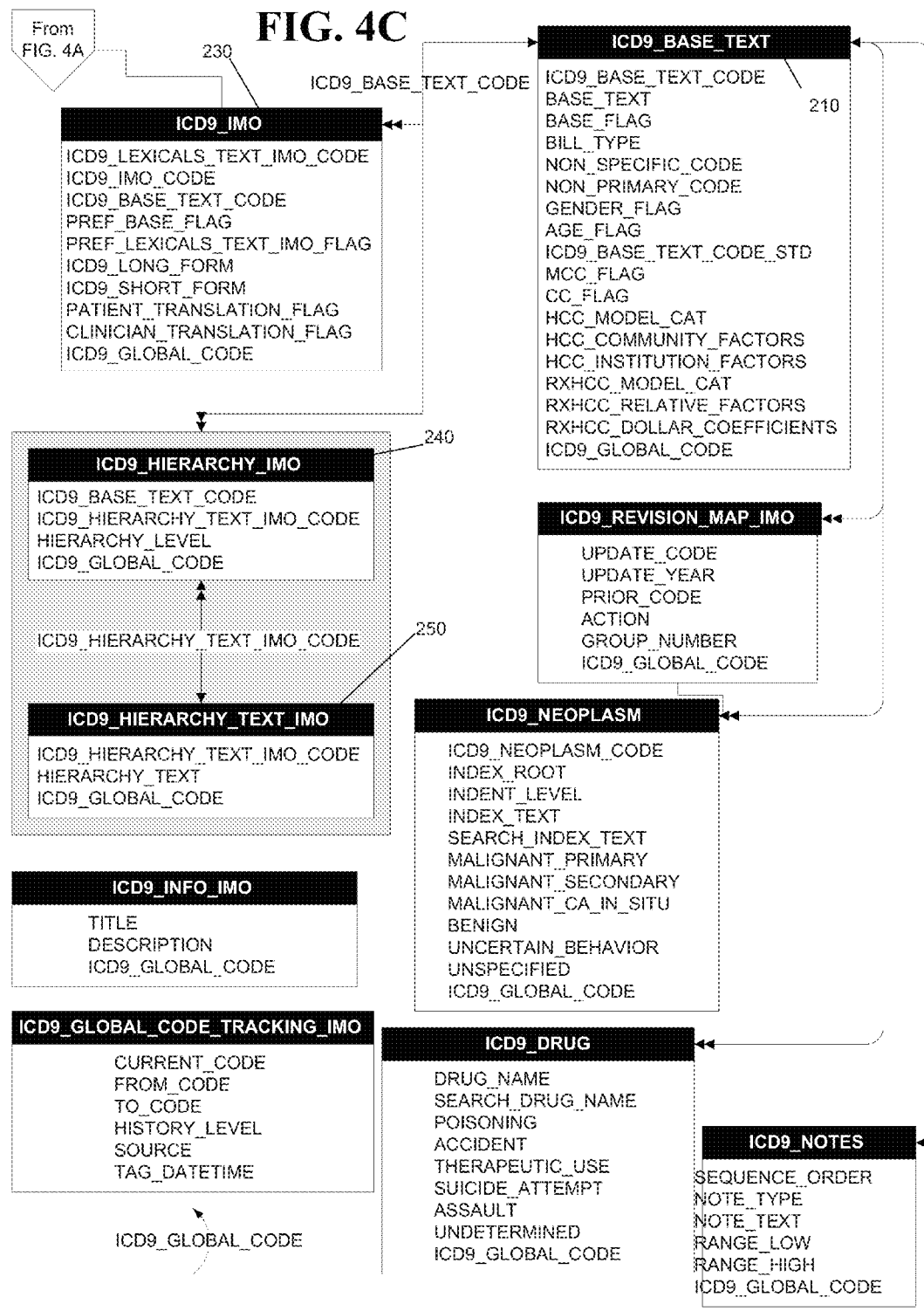

Fracture Type: Closed
- Open
- Closed

Encounter Type: Subsequent
- Initial
- Subsequent
- Sequela

Fracture Sequela: Delayed Healing
- Routine healing
- Malunion
- Nonunion
- Delayed healing

Fig. 5

METHOD AND SYSTEM FOR CONCEPT-BASED TERMINOLOGY MANAGEMENT

BACKGROUND OF THE INVENTION

1. Field of the Invention

The present application is direct to a method and system for managing and implementing one or more external code sets using an interface terminology.

2. Description of the Related Art

One of the challenges facing healthcare computing is the representation of patient data in a usable form. The typical approach is to encode the information using terms taken from a controlled vocabulary. Applications such as CPR's (computer-based patient records), order entry, summary reporting, automated decision support and data aggregation for clinical research all require data to be represented in standard ways if there is to be any meaningful understanding of the data. Understandably, health care providers, educators, researchers, medical and scientific software developers and policy makers often take for granted the existence of an appropriate standard terminology and assume that it is in routine use. In reality, the lack of a standard for representing patient data is one of the today's greatest impediments to medical computing.

The coding of patient information has been carried out long before the advent of computers. This coding typically has been directed at simplifying the data and converting it to a general form that is easier to manipulate and understand. For example, while a patient may have pneumonia that may have been caused by a variety of organisms, involved in different sites in the lung, accompanied by differing symptoms, and of varying levels of severity, coding a patient's diagnosis simply as "bacterial pneumonia" allows it to be aggregated with other cases for statistical purposes, although this coding may lack sufficient specificity for meaningful analysis and treatment.

If finer granularity is needed, more specific terms can be added to the coding scheme (such as gram negative bacterial pneumonia and lobar bacterial pneumonia). A set of patient records can be classified with such codes and then retrieved when cases of certain types are needed. Since this coding represents only a simplified synopsis of information extracted from the record, it may be referred to as abstraction. Record abstraction may be used, e.g., to allow the assessment of incidence of a disease, mortality of a surgical procedure, or cost for a hospital stay.

Documents in a medical field may contain information to which clinical descriptions may be attached, see, e.g., co-owned U.S. publication 2012/0179696, titled "System and Process for Concept Tagging and Content Retrieval."

As computer use has become more prevalent, electronic health records or electronic medical records (EHRs or EMRs) have become the industry standard for documenting patient care. Industry initiatives and government legislation have facilitated EHR implementation and use. Most notable among them is the Health Information Technology for Economic and Clinical Health Act (HIT ECH), which gives incentives to providers toward implementation and demonstration of meaningful EHR use.

An aspect of reliable and accurate information is ensuring that providers have the ability to capture their clinical intentions regarding patient care through terminologies. Healthcare terminology has long been called "the language of medicine," but, in the electronic age, this language has to be readable by both humans and computers. Various terminologies are used in defining associated terms.

Terminology

Terminology is a set of descriptions used to represent concepts specific to a particular discipline. It also is the foundation of EHR data. For example, the terms "heart attack" and "MI" describe the same concept of myocardial infarction. The concept in turn may be associated with codes that are used for a variety of purposes.

Different healthcare terminologies may have their own unique features and purposes. For example, one set of terminologies, RxNorm, encodes medications, while another set of terminologies, e.g., Logical Observation Identifiers Names and Codes (referred to under the trademark "LOINC"), is used for laboratory results.

Terms related to terminology include: Administrative code sets; Clinical code sets; and Reference terminologies.

Administrative code sets may be designed to support administrative functions of healthcare, such as reimbursement and other secondary data aggregation. Common examples are the International Classification of Disease (ICD) and the Current Procedural Terminology, which is referred to via the trademark CPT. Each system may be different, e.g., ICD's purpose is to aggregate, group, and classify conditions, whereas CPT is used for reporting medical services and procedures.

Clinical code sets have been developed to encode specific clinical entities involved in clinical work flow, such as LOINC and RxNorm. Clinical code sets have been developed to allow for meaningful electronic exchange and aggregation of clinical data for better patient care. For example, sending a laboratory test result using LOINC facilitates the receiving facility's ability to understand the result sent and make appropriate treatment choices based upon the laboratory result.

A reference terminology may be considered a "concept-based, controlled medical terminology." The Systematized Nomenclature of Medicine Clinical Terms (referred to under the trademark "SNOMED CT") is an example of this kind of terminology. It maintains a common reference point in the healthcare industry. Reference terminologies also identify relationships between their concepts. Relationships can be hierarchically defined, such as a parent/child relationship. The reference terminology contains concept A and concept B, with a defined relationship of B as a child of A. SNOMED CT includes concepts such as heart disease and heart valve disorder, and their defined relationship identifies heart valve disorder as a child of heart disease.

Reference terminology may allow healthcare systems to get value from clinical data coded at the point of care. In general, reference terms may be useful for decision support and aggregate reporting and may be more general than the highly detailed descriptions of actual patient conditions. For example, one patient may have severe calcific aortic stenosis and another might have mild aortic insufficiency; however, a healthcare enterprise might be interested in finding all patients with aortic valve disease. The reference terminology creates links between "medical concepts" that allow these types of data queries.

An important aspect of a well-constructed terminology is concept orientation, typically granular by nature and defined as "a unit of knowledge or thought created by a unique combination of characteristics." An example of a SNOMED CT concept is aortic valve disorder. A concept may have multiple subconcepts arranged in a hierarchical relationship.

Many clinicians are required to use administrative coding sets (CPT, HCPCS, and ICD-9-CM code sets, etc.) to capture clinical data. However, administrative code sets were designed either to group diagnoses and procedures or to contain broad categories with administrative technical terms with complex rules and guidelines. Examples of this are time durations or vascular branch orders directly stated in various terms.

Administrative codes and terms typically use language that is not natural or familiar for clinicians. For example, in ICD-10-PCS the root operation term "extirpation" is not routinely stated by surgeons. Administrative codes and descriptors also do not contain the different clinical, administrative, and colloquial terms used in healthcare, making it difficult for clinicians, information management professionals, and patients to find the terms they need when performing simple text searches. This disconnect between clinician language and coding sets creates concern over losing clinical intent in the documentation. In addition, forcing a physician to document in administrative terms is uncomfortable and disruptive.

EHR solutions incorporating these terminologies may be limited in providing full value to hospitals and physicians, which may include not delivering meaningful use and full reimbursement levels. These problems may present themselves in various ways. For example, when charting, doctors may be unable to find the correct diagnosis and instead may use free text or may give-up and omit the problem altogether. In turn, this may lead to incomplete and incorrect patient documentation as well as the loss of ability to analyze and report on this information. Lost time and money may result due to under-coding or rejected claims, and the captured information may be useless for meaningful communications with patients and other care providers.

What is needed is a system and method that addresses one or more of the issues and shortcomings presented above.

BRIEF SUMMARY

In one aspect, a method for implementing an interface terminology is described, the interface terminology comprising concepts and descriptions, a description being an alternative way to express a concept. The interface terminology also may include a plurality of domains, wherein each concept is unique within a domain. The method may include the steps of: storing a plurality of concepts in a database; storing a plurality of descriptions in a database; linking each description to a respective concept; storing an external code set in a database, the external code set comprising a plurality of external codes; and mapping an external code to a concept. The method also may include the step of assigning a unique numerical identifier to each concept. The method further may include storing patient data in an electronic health record using the interface terminology.

The external code set may be one or more of an administrative terminology, a clinical terminology, and a reference terminology.

The mapping step may include indicating a type of relationship between the external code and the concept, the relationship being, e.g.: same-as, broader-than, or narrower-than.

At least one concept may include a preferred clinician term and a preferred patient term linked as descriptions of that concept.

The method also may include abstracting similar descriptions for two concepts, such that the descriptions are different.

In addition, the method may include deploying a front-end file of the result of the mapping step, the front-end file comprising a link between the descriptions and the external code set. The front-end file may have a comma-separated-value ASCII format, a tab-delimited ASCII format, a database export format, or a binary flat file format. Additionally or alternatively, the deploying step may involve a cloud deployment that relies upon a stateless, in-memory database.

In another aspect, a method for implementing an interface terminology in at least one database is described in which the interface terminology may include a plurality of concepts and a plurality of descriptions, a description being an alternative way to express a concept. The method may include the steps of: generating a concept table including a column storing a plurality of concept identifiers; generating a description table including a column storing a plurality of description identifiers; linking the concept table to the description table; generating an external vocabulary table including a column storing a plurality of external vocabulary identifiers; and linking the concept table to the external vocabulary table.

The step of linking the concept table to the external vocabulary table may include: generating a mapping table; linking the concept table to the mapping table; and linking the external vocabulary table to the mapping table. The mapping table may include mappings between multiple concepts in the concept table and one external vocabulary identifier in the external vocabulary table. Additionally or alternatively, the mapping table may include mappings between one concept in the concept table and a plurality of external vocabulary identifiers in the external vocabulary table.

The step of linking the concept table to the description table may include: generating a mapping table; linking the concept table to the mapping table; and linking the description table to the mapping table. The method further may include generating a description-external vocabulary mapping table, linking the mapping table to the description-external vocabulary mapping table; and linking the external vocabulary table to the description-external vocabulary mapping table. The description-external vocabulary mapping table includes at least one column from the mapping table and at least one column from the external vocabulary table.

The method further may include the step of: generating a deployment file, the generating step comprising: referencing the description-external vocabulary mapping table; and populating the deployment file with a plurality of entries, wherein each entry links a description with an external vocabulary identifier.

In still another aspect, a method for implementing an interface terminology is described, wherein the interface terminology comprises a plurality of concepts and a plurality of descriptions, a description being an alternative way to express a concept. The method may include the steps of: linking, in a database, each description to a respective concept; storing, in a database, an external code set comprising a plurality of external codes; mapping each concept to a respective external code; and deploying a front-end file, the front-end file comprises a link between the descriptions and the external code set.

The method also may include: adding a new description for one of the concepts; linking the new description to the concept; and re-deploying the front-end file, the front-end file comprises a link between the new description and a code in the external code set. The re-deploying step may occur without the need to re-map the concept to its respective external code.

Additionally or alternatively, the method may include: adding a new external code; mapping at least one concept to the new external code; and re-deploying the front-end file, the front-end file comprising a link between at least one description and the new external code. This mapping step may occur without the need to re-link the at least one description to the at least one concept.

Each concept resides in a domain, and each external code in the external code set may maps to concepts in one or more domains. In addition, each concept may include a description that is the same as that concept.

As part of implementing the interface terminology, patient data may be stored in an electronic health record using the interface terminology.

These and other features and advantages are described in the following description, with reference to the accompanying drawings.

BRIEF DESCRIPTION OF THE SEVERAL VIEWS OF THE DRAWINGS

FIGS. 4A-4C (collectively "FIG. 4") are a database entity relationship diagram illustrating one example of interface terminology including an external code set.

FIG. 5 is a screenshot of multiple drop-down menus for receiving user input when mapping concepts.

DETAILED DESCRIPTION

Many terminologies are required in today's healthcare environment, including one or more administrative code sets, one or more clinical code sets, and one or more reference terminologies. This may result in multiple coding systems being used in a single patient's electronic record and may create an environment where the disparate systems must exchange as well as understand information to provide an effective, integrated healthcare system. Over the life of the patient, modifications or updates may be made to one or more of the terminology groups, further compounding the complexity and need for a comprehensive system configured to recognize multiple terminologies and to communicate those to other terminologies.

In order to provide patient-centered care, providers should be able to document patient care with sufficient clinical specificity. Sound EHR practices allow providers to engage in a patient's care delivery effectively because electronic documentation supports patient-centered care in multiple fashions, most notably for decision-support capabilities and the exchange of data across providers and settings. An important aspect of patient-centered care is having access to dependable data in order to make sound decisions. Accurate and reliable information in an electronic format requires all stakeholders to be engaged with the record. However, forcing a physician to document in administrative terms may be uncomfortable and disruptive.

As described herein, interface terminology may bridge the gap between information that is in the clinical user's mind, i.e., the clinical intent, and information that can be interpreted by computer applications. Interface terminology may help clinicians find the right diagnosis and procedure terms to document and code more comprehensively and accurately within their normal workflow.

Figure 1:
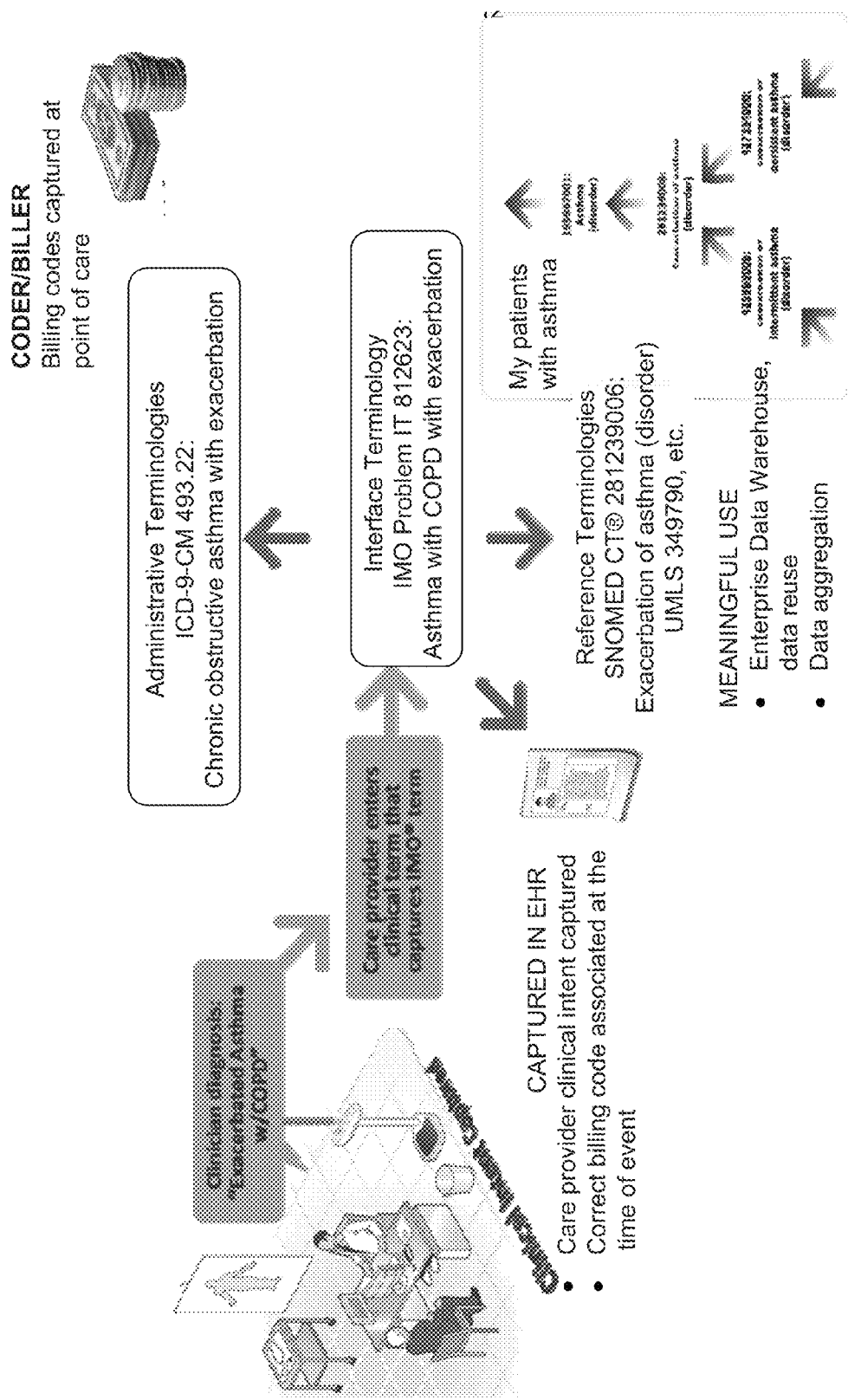
FIG. 1 is a depiction of the medical business processes linking interface terminology and data flow in a medical environment.

As shown in FIG. 1, a clinician's intent may be entered into a system. Via external links to the interface terminology 10, that clinical intent may be linked to one or more external codes sets, e.g., administrative terminologies 20 such as ICD-9-CM, reference terminologies 30 such as SNOMED CT, and clinical terminologies (not shown). Linking to the administrative terminologies may allow for more efficient and accurate completion of various administrative tasks, such as billing. Linking to a reference terminology may allow for meaningful use, such as patient data aggregation and analysis. In addition, via the interface terminology, the patient's EHR 50 may be populated with an entry reflecting the clinician's intent, which may lead to more accurate and thorough treatment, proper billing codes for more precise billing, and clinical data for improved research and analysis.

Terminology is important in many fields, particularly in the medical field, where very specific information may be required to provide a proper diagnosis for evaluation and treatment or a complete medical record for accurate analysis of a patient's history. To this end, medical records are faced with two competing problems: without sufficient specificity, the user may not be able to record accurately what is needed for quality patient care and may be "forced" to say something that is not quite correct. Conversely, the higher the degree of granularity or specificity, i.e., the greater the number of concepts, the larger and more unwieldy the system may become. This also may lead to unnecessary variation, where multiple concept entries exist for what fairly should be considered the same concept.

The method and system of applying the interface terminology 10 described herein may manage these competing interests by employing a set of clinically relevant terms mapped to one or more other code sets, which may include internal or external code sets and further may include industry standard administrative and clinical code sets and reference terminologies. Clinically relevant terms capture granularity and clinical intent in the documentation.

Interface terminology may include multiple components, including: Domains, Concepts, Descriptions, and Words. As discussed below, there may be relationships among elements within each of these components, as well as between elements within each component, which may be described as granularity. More information about interface terminology may be found in the co-owned U.S. publication 2012/0179696, titled "System and Process for Concept Tagging and Content Retrieval," which is referenced in the Background above, and the contents of which are incorporated herein by reference.

Domains

A domain may be the uppermost level of the hierarchy. Each domain may be a container for one or more concepts. Domains may include, e.g., problems, procedures, diagnoses, medications, allergies, family history, observations, etc.

Concepts

Concepts may be one step down from domains and may be considered containers for descriptions. A concept may define a clinical finding and may be a fully, well-defined expression of clinical intent. It may be unambiguously defined and may reside within a single domain.

A concept may be a coded entity with unique semantics. While concepts may reside higher up in the order of terminology specificity, concepts preferably are specific enough to provide accurate, unique terminology for a user.

Adding a concept may require creating a concept description (more specific) and domain (more general) for the concept. The concept description may be added as a default description for the new concept. Each concept description preferably is unique for the domain to which the concept pertains, although a single concept may appear in multiple domains.

The existence and status of concepts preferably is fluid and subject to change or user modification. For example, while not limited to or necessarily encompassing each of these options, concepts may be added, updated, deleted, retired, or merged.

When updating or otherwise modifying the status of a concept, the system may establish an audit trail of all modifications.

Deleting a concept may require deleting all maps associated with the concept.

Retiring a concept may include removing relationships to that concept and affecting the status for that concept. The status may be modified to reflect the retired status. This status may occupy a row in a table listing each of the concepts.

Instead of deleting or retiring a concept, it may be desirable to merge one or more concepts together. In the event of merging an older concept with a newer concept, the user preferably is able to search for the newer concept. In addition, data associated with the older concept may be re-mapped to the newer concept ID. A row in the concept table for the older concept may be flagged as retired, and a comment may be inserted to reflect that the older concept has been merged with the newer concept.

Conversely, instead of merging concepts, it may be desirable to keep one or more concepts distinct from one another but create a relationship between the concepts. For example, a single concept may be split into one or more additional concepts, and it may be desirable to indicate that the multiple concepts are related. This is achieved by creating and maintaining qualified concept-to-concept relationships, e.g., "is a child of," "is a parent of," etc.

In order to keep track of concepts, each concept may be assigned a unique numerical identifier. This identifier may be generated randomly. Alternatively, multiple related concepts may share some commonality in identifiers, e.g., each having the same first three numbers.

Each concept may map to one or more external codes (e.g., a reference, clinical, or administrative terminology), where each mapping indicates both: a) a preferred status and b) a type of relationship in comparison to the external code, e.g., same-as, broader-than, or narrower-than. For example, the concept "acute mastoid sinusitis" may have a preferred map to a SNOMED concept of "acute sinusitis" with a relationship type of "narrower-than," meaning that the concept being mapped is "narrower-than," i.e., more specific than, the SNOMED concept. It may be desirable to map the new concept to a reference terminology or to one or more other concepts, either at the time of creation or otherwise.

Clinical interface terminology may use a reference terminology to create or supplement ontology, i.e., relationship among concepts.

Categories

The system may allow for the creation of categories, which may not be related hierarchically to the other system components. Each category may have one or more concepts mapped to it. Categories may be a sub-domain, e.g., laboratory procedures within a "procedures" domain, or a collection of concepts across sub-domains.

It may be possible to add new categories, delete an existing category, or edit the name of an existing category. New categories may have unique names and may have associated comments. In one embodiment, only the user that creates a category may be allowed to delete that category. In another embodiment, either that user or a user with higher access privileges may be able to delete the category. Deleting a category may result in the deletion of all concepts mapped to that category.

Within a category, the user may be able to add one or more concepts to the category. Conversely, the user may be able to add one or more categories to a concept or to delete a category from a concept.

The system also may allow for the copying of one or more concepts of an existing category to another category or a new category.

The user also may be able to able to add one or more flags to a concept and/or the concept-description mapping. With respect to that mapping, flags may be used to associate the concept with, e.g., a default description, preferred descriptions, consumer descriptions, secondary descriptions, etc. In addition, a flag may be used to indicate whether the concept or one of its descriptions is a lingual variant, e.g., and English/British variant. Flags also may be used to establish search filters and/or display result filters, e.g., only displaying terms relevant to one or more groups of users.

Descriptions

Descriptions may be a collection of text strings or terms and may represent alternative ways to express a concept, which may allow the system to capture concepts in the terms that various, varied practitioners may use. Multiple descriptions may map to a concept, but each description preferably has the same meaning. For each concept, there may be one or more preferred descriptions. For example, there may be at least one of a preferred clinician and a preferred patient term, in order to capture both clinical intent and an explanation understandable by the lay patient. As discussed above, preferred terms may be called out with the use of flags to the respective entries.

It may become necessary to determine whether a new term is a description within an existing concept or whether it merits the creation of a new concept. This determination may be driven by an iterative, editorial process. Preferably, the determination is based on an understanding of clinical science, such that creation of a new concept results from a clinical understanding of its difference as compared to existing concepts.

Each concept may include a default description, and the system may include an editing module in order facilitate changing this description. A default description may be selected, e.g., by receiving a user selection, and it may be the description that is mapped to a concept and has a CONTEXT_ID equal to some predetermined value, e.g., 1. While descriptions may be deleted, the system may prevent the deletion of a default description, at least until a new default description has been established.

Figure 2:
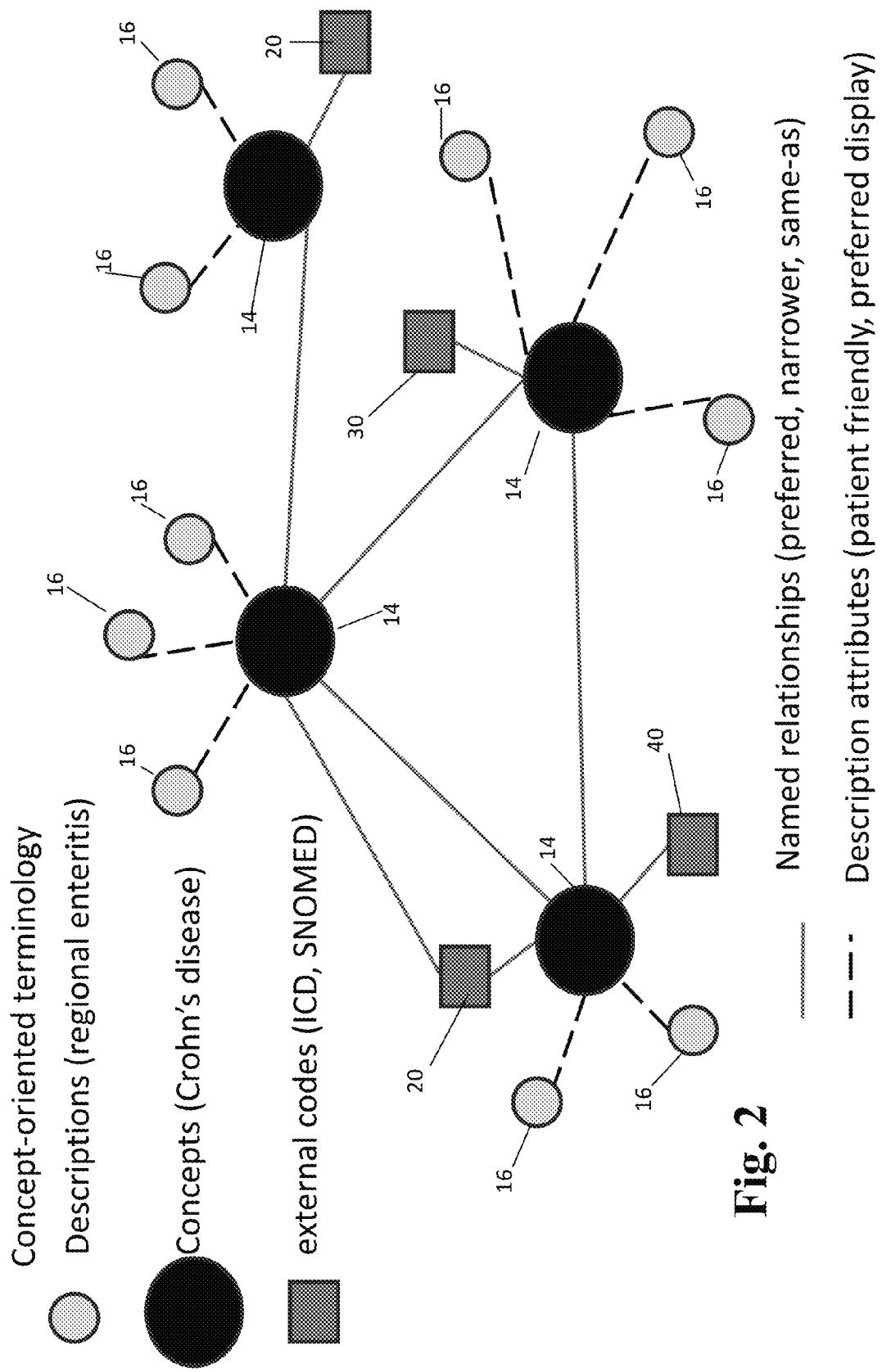
FIG. 2 is a representation illustrating one example of the relationship between concepts and descriptions within an interface terminology and external codes linked to the terminology.
Figure 3A:
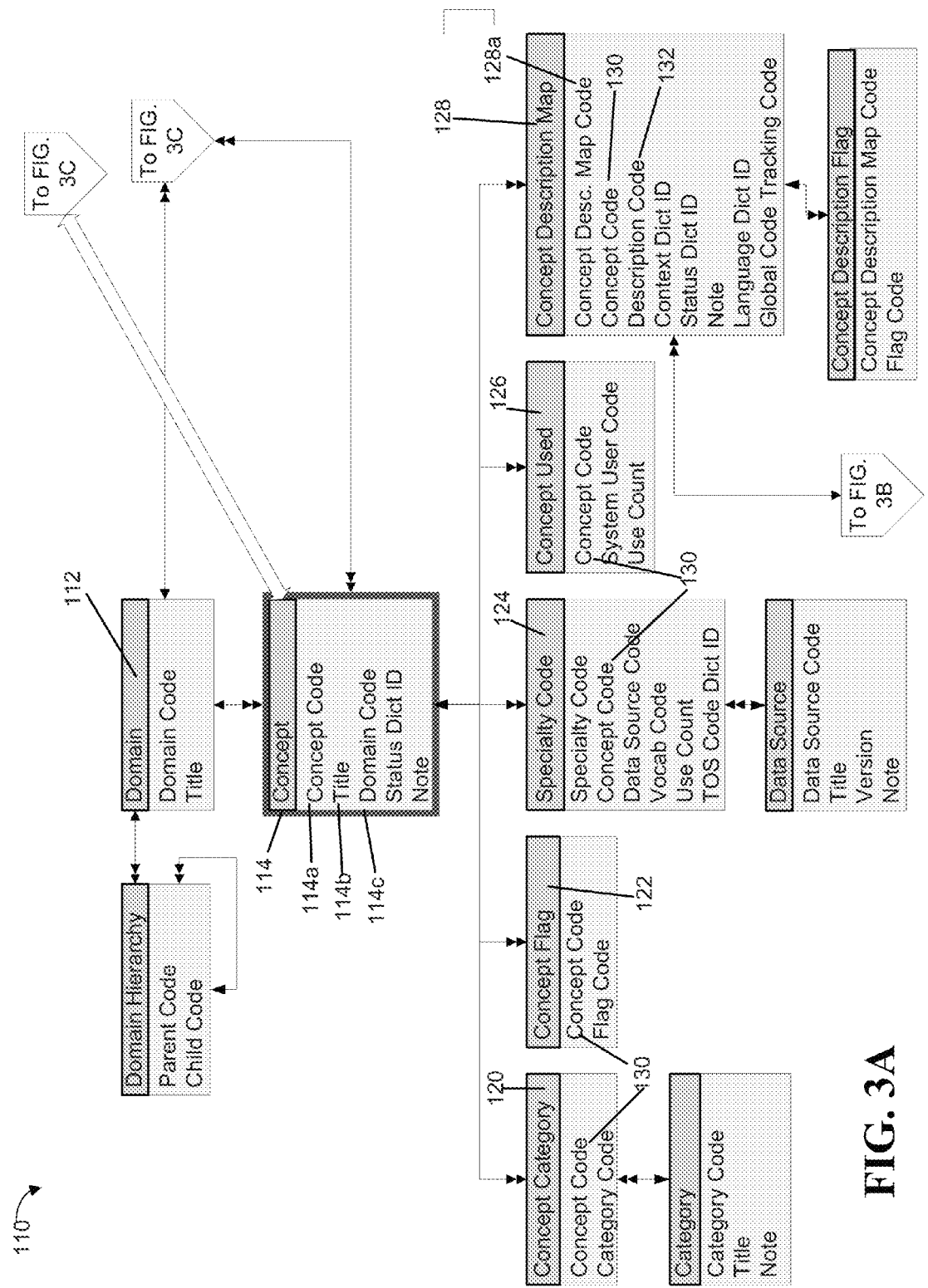
FIGS. 3A-3E (collectively "FIG. 3") are a conceptual database schema diagram depicting the relationship between elements of an interface terminology and the mapping to elements of an external code set or vocabulary.
Figure 3B:
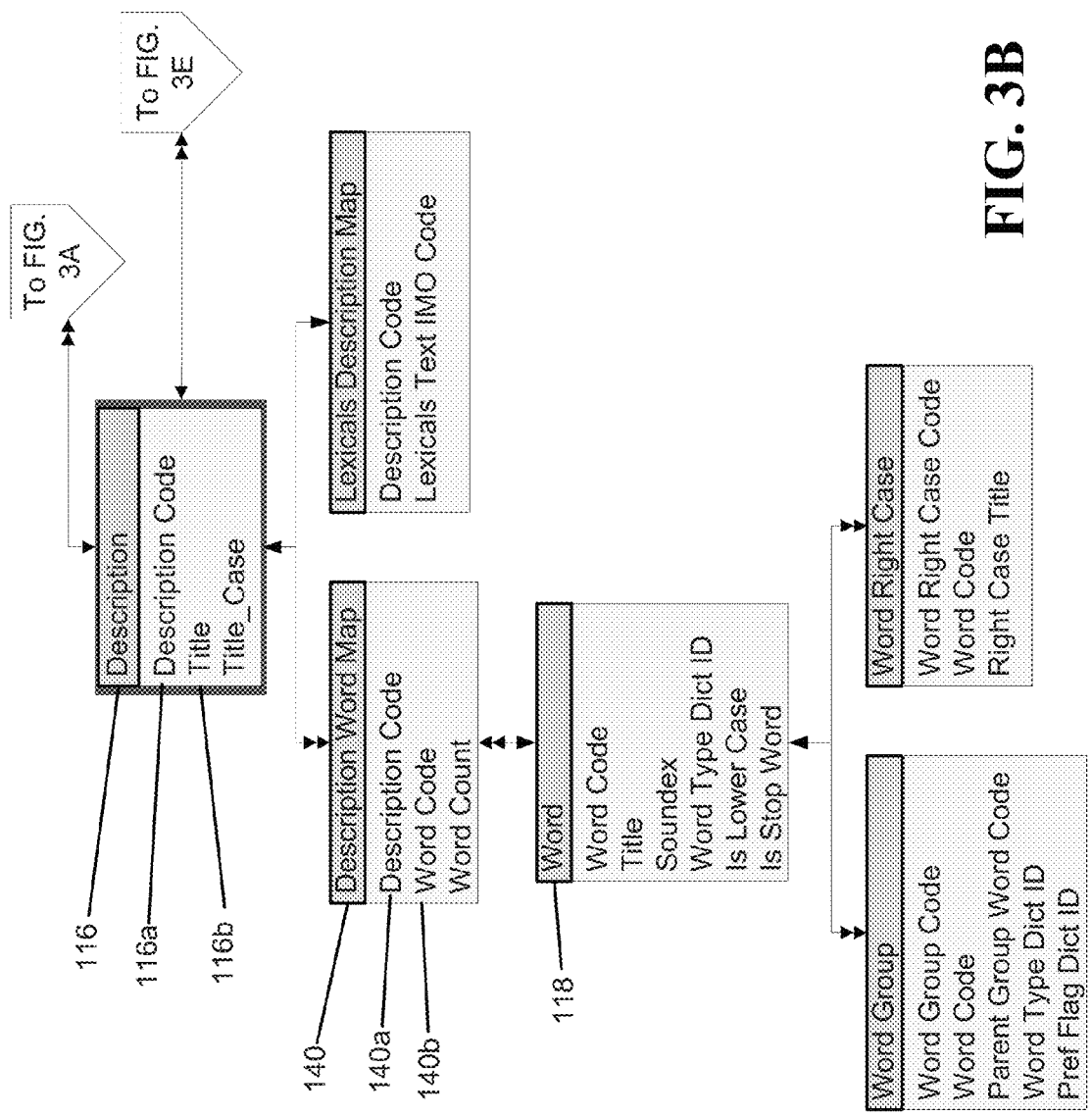
Figure 3C:
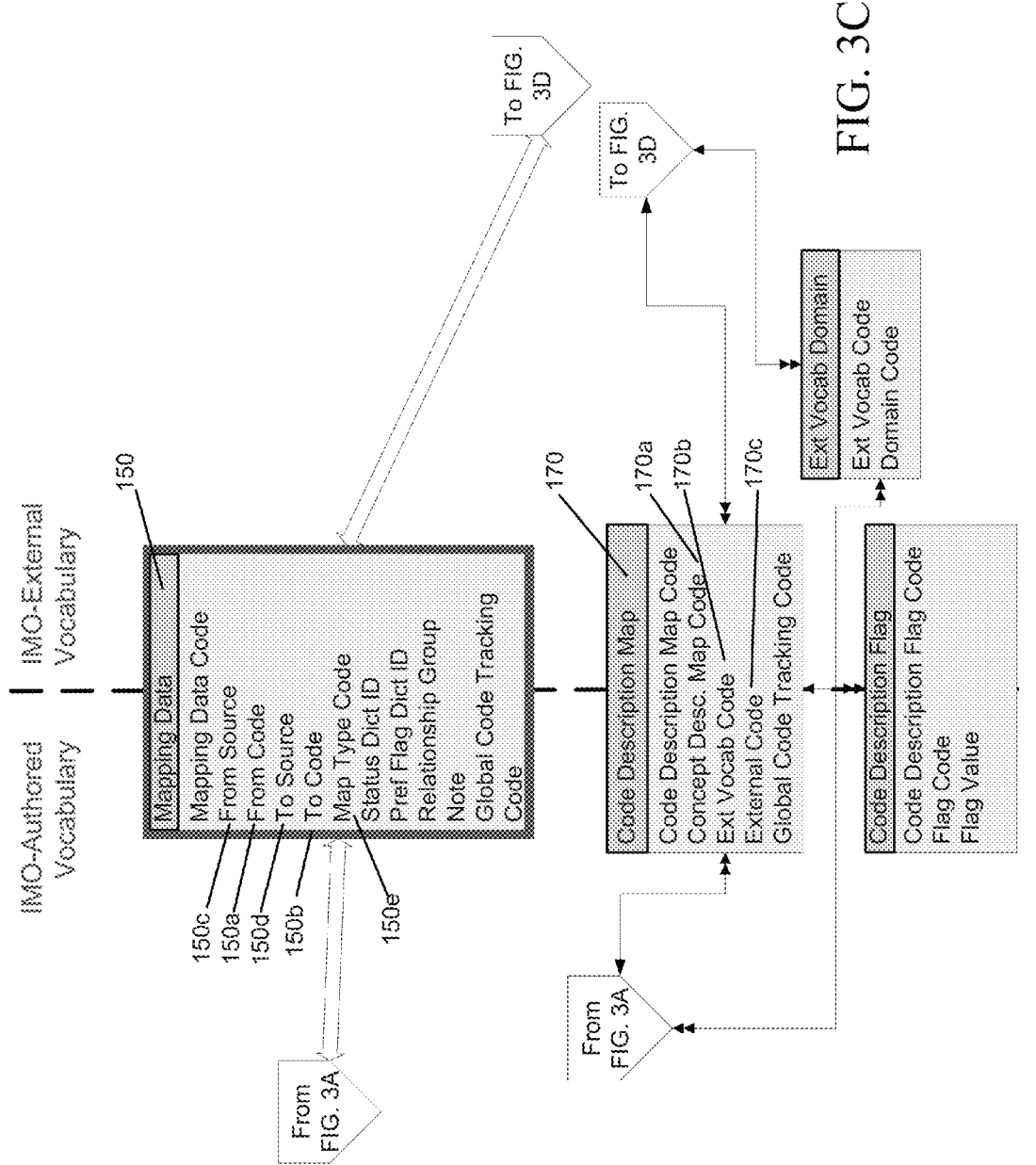
Figure 3D:
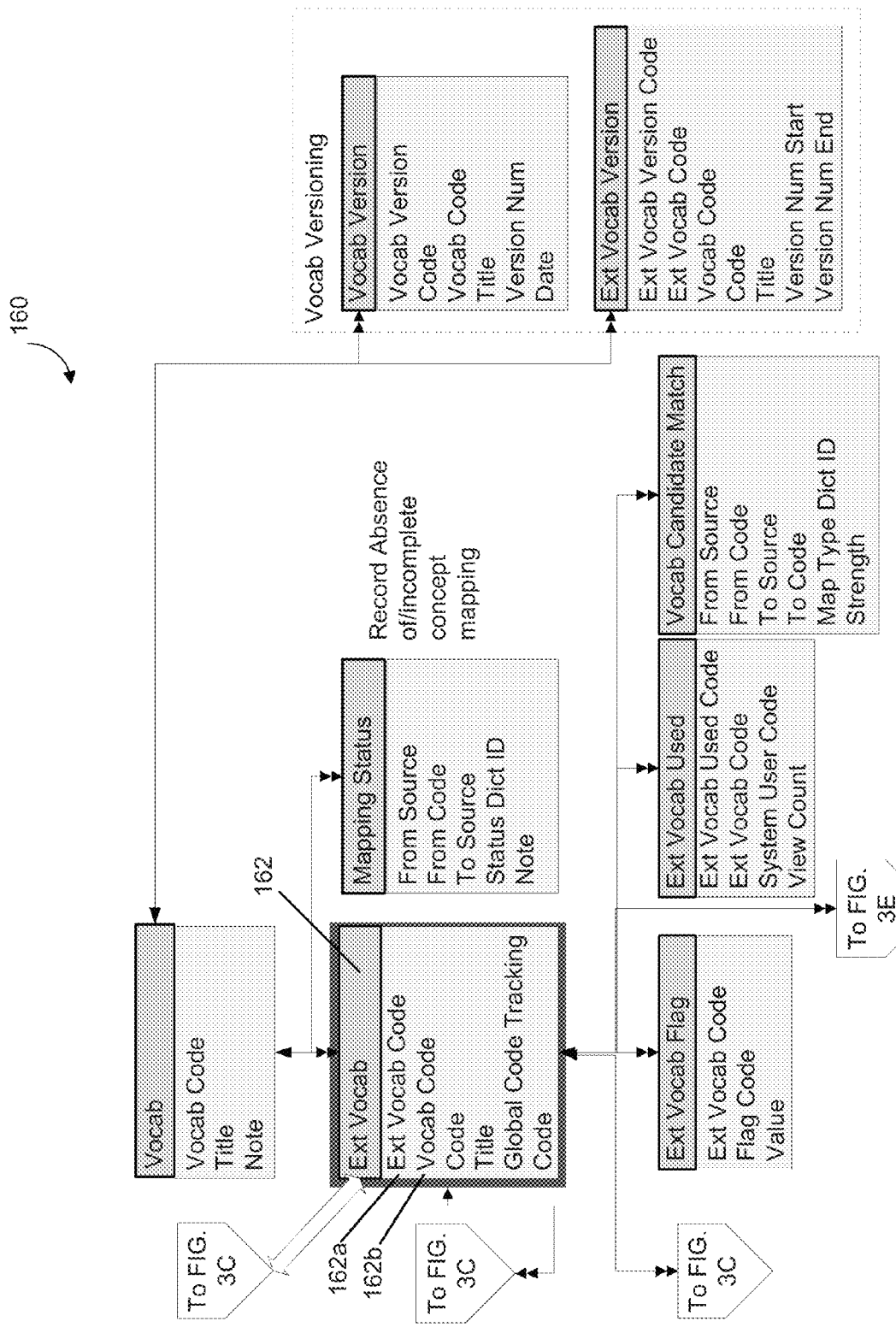
Figure 3E:
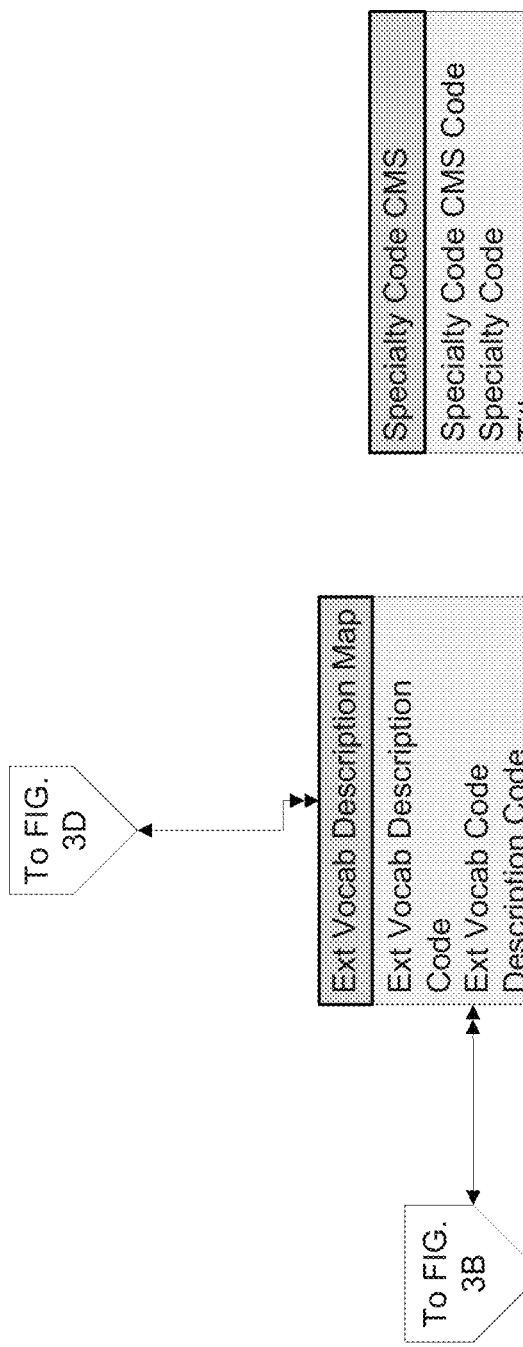

As seen in FIG. 2, multiple descriptions 16 may be associated with each concept 14. Descriptions 16 are associated with lists of words (discussed below). (FIG. 2 further illustrates that each concept may map to one or more external codes, such as an administrative term code 20, a clinical term code 30, and/or a reference terminology code 40.) These words may include the words that map to descriptions 16 from a table such as the DESCRIPTION_ WORD_MAP table. They also may include words that map to words in one or more other tables, such as a WORD_ GROUP table, which may include other variations around the word, e.g., plural forms and misspellings.

Concepts are unique within a domain, and the same description is not used more than once across all concepts. Thus, the system may allow the user to leverage existing descriptions to form the basis for new descriptions. For example, the system may include a graphical user interface that allows the user to select an existing description within a separate concept and to populate fields relating to the description in the new concept with those from the existing descriptions. Similarly, selecting an existing description within the same concept or a different concept may generate a list of suggested descriptions to be added based on word equivalence. Moreover, instead of copying a description from one concept to another, the system may allow the user to move a description between concepts.

Without context, a description may not provide the user with full understanding of what it represents since the description may be related to multiple concepts. For example, acronyms may be included as descriptions, and while the acronym MI may refer to myocardial infarction or mitral insufficiency, descriptions may be "MI (myocardial infarction)" and "MI (mitral insufficiency)," which may be referred to as disambiguation. Even if the same description is used in multiple concepts, preferably the system includes a separate instance of that description for each concept. For example, two of the concepts shown in FIG. 2 may include the description "MI," but those descriptions 16 are linked to their own concepts 14, i.e., there is no description that shows a relationship with two separate concepts.

Words

Words may be a subset within descriptions. Words may reflect variations of the descriptions such as misspellings, alternative spellings, abbreviations, variations in parts of speech (the adjective of a noun description, e.g.), etc.

Words also may include items that are related to, but are not variations of, the descriptions to which they are attached. For example, "heart" may be a word under the description "myocardial infarction."

The left half of FIG. 3 illustrates one example of the relationships between the domain 112, concept 114, description 116, and word 118 component tables of an interface terminology schema 110. The arrowheads in this figure represent the degree of relationship; thus a line with one arrowhead pointing to one table at one end and two arrowheads pointing to a second table at a second end depicts a one-to-many relationship.

As seen in FIG. 3, each concept table 114 may include an entry in columns representing the concept code 114*a*, title 114*b*, and domain code 114*c*. The concept additionally may include entries in the Status Dict ID and Note columns.

Concept table 114 may link to one or more additional concept-related tables 120, 122, 124, 126, 128. One or more of these tables may include a column containing the unique identifiers for each concept, e.g., "Concept Code" column 130. Concept code column 130 may be identical to or relate back to concept code column 114*a*, e.g., via the use of one or more foreign keys to refer back to the parent concept table 114.

Similarly, each description in description table 116 may include entries in at least a description code column 116*a* and a title column 116*b*. The schema shown in FIG. 3 indicates that there may be a table linking the concepts to the descriptions, e.g., the "Concept Description Map" table 128. Within this table, there may be columns for concept codes 130 and description codes 132, as well as a column for a code indicating a map 128*a* between concepts and descriptions. Because multiple descriptions may map to a single column, entries in the description column preferably are unique, whereas entries in the concept column may be repeated. Alternatively, entries in each of the concept description map code, concept code, and description code columns may be unique, and for each map code entry, there may be pointers to the respective entries in the concept code and description code columns.

Staying with FIG. 3, similar relationships exist between the description 116 and word 118 tables, with both linking to a Description Word Map table 140 that includes both description code columns 140*a* and word code columns 140*b*.

Interface Terminology

Within this framework, an interface terminology 10 may be created. An interface terminology may be the link between what the clinician wants to say and what the terminology can capture.

Unlike administrative code sets and reference terminologies, which often are stored in the back-end functions like billing, reporting, decision support, research, and interoperability between applications, an interface terminology may operate at the front-end of a clinical information system, i.e., in the "presentation layer."

The interface terminology may be a suite of vocabulary products that help institutions capture clinical patient information. This interface terminology subsequently may provide access to standardized vocabularies, such as ICD, CPT, SNOMED® CT, MeSH, & UMLS, in order to connect providers and patients with the patient record, administrative information, academic references, and consumer information. As such, an interface terminology may serve multiple ends, including, e.g., capturing a clinician's intent, driving financial aspects including billing, and driving analytical functions.

In one embodiment, an interface terminology may include mappings between concepts and code sets that are configured not to change over time. Alternatively, the mappings between an interface terminology concept and a reference, interface, or other standard code set may be subject to change, e.g., in light of regulatory changes or modifications to those code sets.

A key feature in establishing an effective terminology may be the inclusion of a comprehensive set of descriptions for each concept. Descriptions preferably include both clinician-friendly terms, e.g., vernacular, common terms, abbreviations, acronyms, eponyms, or common misspellings, and patient-friendly-terms.

Relationship to Electronic Medical Record

The present system may be integrated within an EMR, see, e.g., commonly owned U.S. Publication 2008/0065452, titled "Longitudinal Electronic Record System and Method," the contents of which are incorporated by reference, such as by linking external codes with interface terminology related to data in the various instances within a medical record.

The system also may be separate from the EMR, and the EMR may access the terminology as an external service.

A patient's medical record may include multiple domains of terminology, including, e.g., problems, plans, procedures, observations, histories, allergies, medications, etc. Each of these domains will include sets of concepts that may be mapped internally to other concepts and externally to other codes or source vocabularies.

Unique concepts may belong to, at most, one domain. Domains may be divided into sub-domains. In one embodiment, concepts map to external code sets. For example, problem concepts may map to administrative code sets, such as: ICD-9-CM, ICD-10-CM, ICD-10-WHO, ICD-10-CA. Procedure concepts may map to administrative code sets, such as: CPT, ICD procedures, and HCPCS. Observation concepts (including, e.g., lab results) may map to LOINC. Other external source vocabularies for mapping may include, but not be limited to, e.g., UMLS Metathesaurus, NCI Thesaurus, NDC or other drug terminologies or codes, nursing terminologies such as NIC, NOC, NANDA, CCC (previously known as HHCC), and PNDS.

Alternatively, it may be possible to map concepts in multiple domains to one external code set. For example, all interface terminology concepts across multiple domains may map to respective SNOMED concepts.

Concepts may include work flow aspects. For example, concepts may be orderable, performable, resultable, chargeable, and/or historical. (Concepts are flagged as one or more of these aspects, e.g., procedure terms may be used in multiple contexts.) Each of these aspects may relate to external coding or terminology, and the present system and method may link this coding or terminology together.

External Code Mapping

In the past, descriptions may have been mapped to respective codes in external code sets individually. Multiple descriptions may have mapped to a single external code, but those descriptions may not have had the same meaning.

Here, conversely, each description 16 in the interface terminology 10 preferably maps to a concept 14, and that concept 14 is mapped once to the respective codes in the external code sets 20, 30, 40, as seen in FIG. 2. As such, the underlying descriptions may be subject to additions, deletions, or other modifications, while the higher-level concept linking remains intact.

In addition to user-generated matches between system concepts and external codes, the system may populate a list of potential match candidates, e.g., based on word equivalency that meets or exceeds a predetermined or user-defined threshold.

Concepts are related to external code sets using qualified relationships—a relationship type—including: exact match, broader than, narrower than, related to, equivalent to, has-location, has-severity, has-laterality, etc. Other relationship types may include: "due to," "associated with," "has morphology," "has causative agent," "has associated finding," "has laterality," "has associated procedure," "has location," "has direct evidence," "has direct substance," "has focus," "has interpretation," and "interprets." This relationship coding may provide more granular and complete relationships, which may provide a more accurate mapping.

Preferably, the interface terminology concepts are at least as specific as the external codes. In the event that an interface terminology concept is broader than a more-specific external code, that interface concept may map to one or more of the more specific external codes. Alternatively, a newer, more specific interface terminology code may be created, in order to respond to clinical care use cases In a significant majority of cases, the interface terminology concepts may be more specific (more granular) than those of the external code sets. In that case, those concepts may map to the next highest, most accurate external code.

Multiple external code set codes further may be related to a distinct concept according to varying degrees of preference, e.g., primary preferred, primary non-preferred, secondary preferred, or secondary non-preferred.

One concept may map to multiple external codes. Additionally, multiple concepts may map to a single external code. The system may include a preferred base code mapping flag that indicate the optimal external code for a given description and, conversely, a preferred description code mapping flag that indicates which description is preferred for display of a given external concept.

One or more descriptions may be copied from a first concept to a second concept that is part of a different domain. Similarly, code mappings from one concept may be cloned to pertain to a second concept, and the system may permit the user to select which codes to copy.

The system and method may allow for a large degree of flexibility in mapping. For example, it may be possible to map to external codes that include laterality (e.g., one code for a problem relating to the right kidney and a second code for a problem relating to the left kidney). Additionally, the system and method may map to codes that reflect combinations (e.g., Crohn's disease of small intestine with fistula) and codes that reflect a recordation of the episode of care (initial visit vs. follow-up, etc.).

External code sets may be updated or modified fairly regularly, e.g., one or more times a year for most sets and up to weekly or even daily for drug vendor data. This system and method may process these updates in a back-end environment, such that users may continue to use the same terminology, unaffected by these updates.

Data may be stored in one or more databases, e.g., object-oriented or relational databases. Mapping, as well as the ultimate packaging of the mapped relationships into an end-user format as described below, may occur on one or more computers via one or more processors. In addition, while the data structure described herein reflects entries in columns within one or more tables, this should be understood to encompass a data structure with the categories entered in rows.

Returning to FIG. 3, this external mapping may be represented by the creation of a Mapping Data 150 table that links the Concept table 114 on the Interface Terminology side and the Ext. Vocab table 162 on the External Vocabulary side 160. As with the mappings between concepts 114 and descriptions 116, described above, where there is a column for concept codes and description codes, the Mapping Data table 150 may include columns for a "From Code" 150a and a "To Code" 150b, e.g., an interface terminology code and an external vocabulary code, respectively. In addition, because there may be multiple domains storing concepts and multiple external code sources, the table also may include columns with entries identifying a "From Source" 150c and a "To Source" 150d. The mapping table also may include a Map Type column 150e, which may provide additional information regarding the mapping, e.g., whether the mapping is primary preferred, primary non-preferred, secondary preferred, or secondary non-preferred.

Figure 4A:
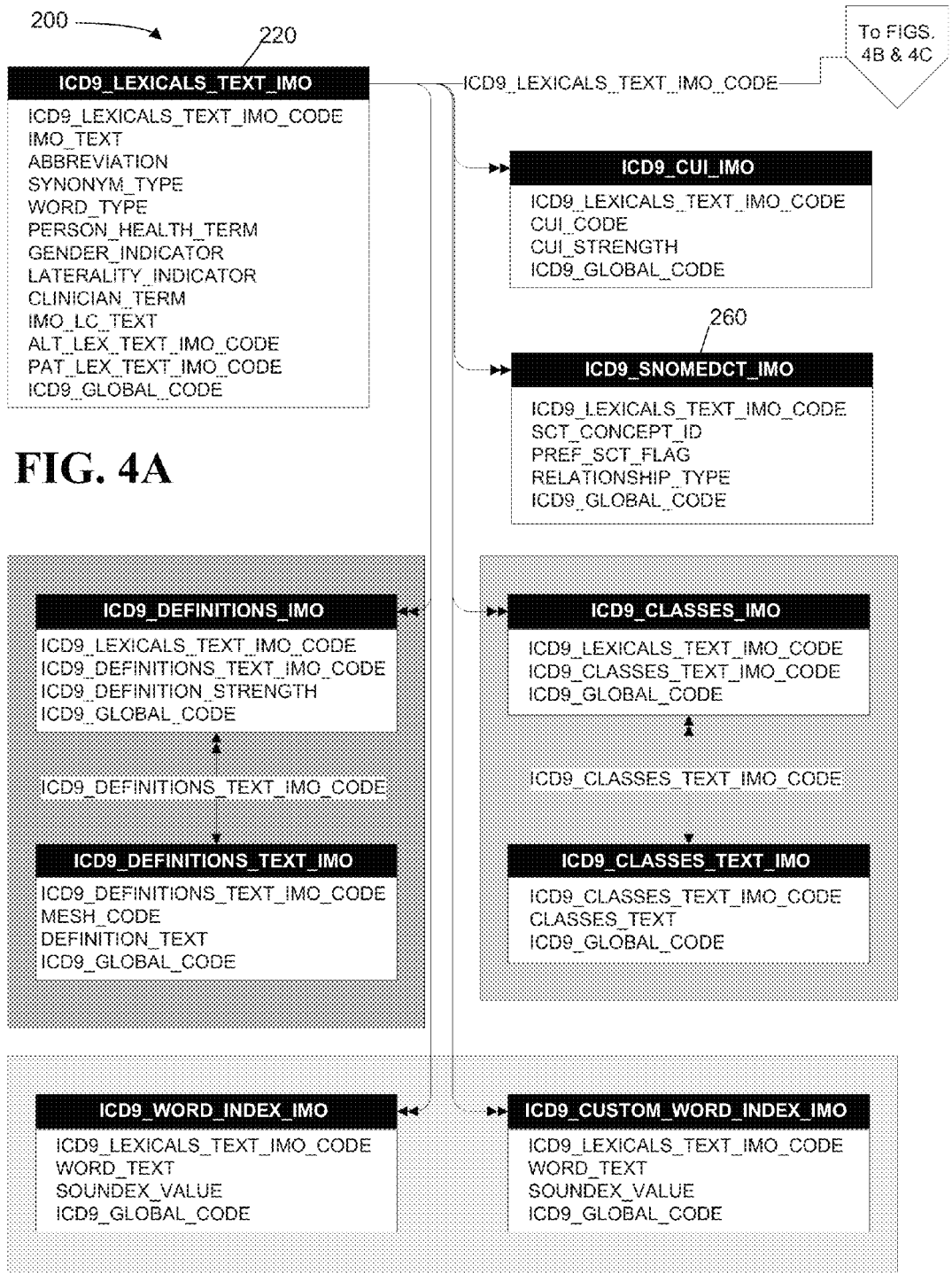
Figure 4B:
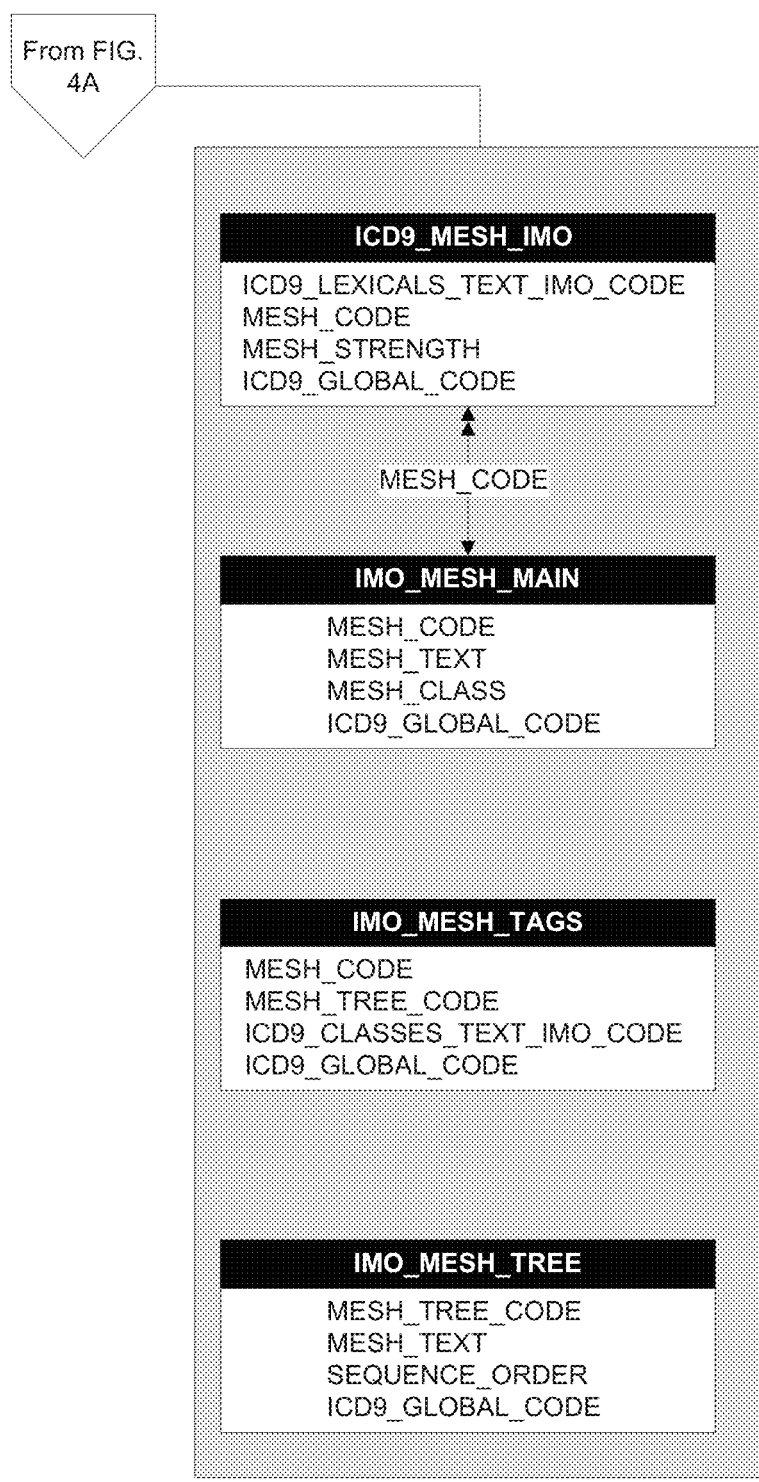

FIG. 4 shows a distribution entity relationship diagram 200 illustrating the relationship between one external code set (here, ICD-9) and the interface terminology. FIG. 4 may not represent a true back-end data structure, such as the one shown in FIG. 3, but instead may reflect how the data may be presented or perceived as a result of a software build from FIG. 3.

Table ICD9_BASE_TEXT 210 may contain the codes and full textual descriptions of the ICD-9 external code. It also may contain a plurality of entries and/or flags for additional information that may be useful with the external code, e.g., ability to bill, code specificity, ability of code to be used as primary diagnosis, gender indicator/flag, and age indicator/flag.

Table ICD9_LEXICALS_TEXT_IMO 220 may include codes and related textual entries for interface terminology descriptions/lexicals.

Linking these tables, table ICD9_IMO 230 may map the interface codes and texts to the external codes and texts in a many-to-many relationship. This table also may include flags to determine preferred codes for each relationship. It also may include flags for the following entries: a match to the external code full description; a truncated short description; a patient translation flag (flagging a preferred patient description); a clinician translation flag (indicated preferred physician description for a given external code); a preferred base code mapping, which indicates an optimal external code for a given description; and a preferred lexical/description code mapping.

In order to manage data, a system and method such as disclosed in the co-owned U.S. Pat. No. 6,904,432, titled "Adaptive Data Manager," and/or U.S. Pat. No. 7,693,917, titled "Method for Adaptive Data Management," may be useful, the contents of both of which are incorporated by reference. For example, elements of the interface terminology and their relationships, as well as relationships with the external code sets, can be captured and managed using a directed graph data structure in a back-end information storage infrastructure.

Other tables in this structure may include a hierarchy table such as ICD9_HIERARCHY_IMO 240, which contains clinical hierarchical designation of each code. There may be multiple levels of designation indicated by the HIERARCHY_LEVEL column in the table. Each external code may have at least one entry in this entity. In one aspect, the actual text for this table may be stored in a separate, linked table, such as ICD9_HIERARCHY_TEXT_IMO 250.

Another significant table may be represented by the ICD9_SNOMEDCT_IMO table 260 of FIG. 4. This table may contain a mapping between interface terminology description terms and external code concept terms. Each description may have one or more maps, although the table may include preferred flags and relationship flags to allow for a one-to-one mapping, if necessary.

IMO Terminology Management Tool

Code mapping may be implemented using a terminology management tool. This tool may be web-based and include a secure login with role-based access privileges. The system may permit users to have more than one role and also to support multiple simultaneous users.

The terminology management tool may include a series of separate panes to perform various tasks or analysis. A jobs pane may allow a back-end user to see if there are any pending jobs that require action, e.g., determining whether a new description warrants its own concept or whether an existing concept should be split into a plurality of concepts. A categories tab may enable the user to add, delete, modify, or otherwise edit one or more sub-domains. A history pane may provide the user with a trail of all changes and all users responsible for those changes.

In addition, the tool may include a search pane in which the user may enter all or a portion of a search phrase. The system may search the database of interface terminologies and also may search the external concepts to determine and display the closest matches to the search term. Preferably, the system may prompt the user to select a relevant domain for searching, so as to narrow the scope of the search.

The system may highlight the top search result and display relevant information about it in the rest of the terminology management tool. This display may be refreshed upon receiving a user selection from among the search results. Because the search results may represent descriptions, the data displayed in one or more of the additional task panes may be related to the selected description's parent concept. Alternatively, the search results may be concept entries, and the displayed data relates directly to the selected concept.

The terminology management tool may allow for the addition, merging, moving, copying, or deleting of a concept, e.g., via the selection of one or more radio buttons.

If the user chooses to add a new concept, the system may prompt the user to enter the new concept name, select the relevant domain, and enter the relevant external code to which the new concept maps. The system may permit the user to search for and select a desired code, e.g., through various search techniques known to those of ordinary skill in the art. The system also may receive a user selection of the mapping type, e.g., "same as," "broader than," or "narrower than." When the new concept is created, the system may generate a first description for that concept that has the same name as that concept. This description may be marked as the default or preferred description, although those designations may be changed once one or more additional descriptions are added.

Continuing with the terminology management tool, the system may display the various descriptions mapped to the selected concept, along with the flags applied to each of those descriptions. Each concept may have a preferred description, which may or may not have the same name as the concept itself. For example, a selected concept of "myocardial infarction" also may include a "myocardial infarction" description, and that description may include a PF context flag to indicate that this description is the preferred choice and a default flag to indicate that it is the default choice.

As discussed above, each interface terminology concept preferably also includes a preferred consumer term in order to communicate the meaning behind the concept to the patient in an effective, less technical manner. The mapping tool may display and permit modifications to this term.

The terminology management tool further may provide a summary of each external code mapped to that concept. The summary may include the source of the external code, the map type (broader-than, narrower-than, etc.), the number corresponding to the external code, and a description of that code. More than one external code may include a preferred designation, although preferably only a single code within each external code set includes such a designation. For example, a concept may map to one ICD-9-CM external code and multiple SNOMED CT external codes. The system may apply a preferred designation to both the ICD-9-CM and one of the SNOMED CT code, while not designating the other SNOMED CT concept as preferred.

The system may include an auditing subsystem to track creations and edits to the data. For example, created and edited data may include a date and/or time stamp, as well as a record entry corresponding to the user ID of the user that made the additions or modifications. In addition, the system may include the ability to rollback changes to one or more previous states.

Internal Concept Mapping

Returning to FIG. 2, multiple concepts may be related to one another and should be linked to reflect these relationships. A simple form of relationship may be, e.g., a parent-child relationship between two concepts. Other, more complex relationships, e.g., broader than, narrower than, has-location, has-severity, and has-laterality, also may exist amount various concepts.

Additionally, code mapping may support clinical and non-clinical modifiers. Clinical modifiers may relate to the substance of the term being coded, e.g., when coding a fracture, clinical modifiers may include "open," "closed," "compound," etc. Modifiers may be maintained as concept qualifiers, which may be deployed in run time. Conversely, non-clinical modifiers may provide additional important information, but that information may be less related to the substance of the term. For example, the system may include non-clinical modifiers for the type of encounter during which the code is captured, e.g., "initial," "subsequent," "etc."

The system may present the user with variations on the entry point concept to select, e.g., displaying "fracture of surgical neck of right humerus," "open fracture of surgical neck of right humerus," and "compound fracture of surgical neck of right humerus" on the same screen. The system then may receive a user selection of the desired concept.

Alternatively, the system may display the base concept to the user and then provide the user with one or more menus from which to select the desired modifiers. For example, once the user enters his or her clinical intent, the system may display various possibilities for the user to select. Using the example in the preceding paragraph, the user may select "fracture of surgical neck of right humerus." Turning to FIG. 5, at that point, the system may display one or more drop-down-type menus, e.g., one for a clinical modifier (e.g., fracture type), a second one for encounter type, and a third for a status (e.g., sequela). The system then may receive the user's selections of the desired modifiers, building the complete entry in that manner.

Clinical Workflow

Clinicians interact with interface terminology when documenting diagnoses and procedures in the patient's electronic record. The user, e.g. a physician, may perform searches using a search functionality in designated locations in an EHR. The search terms may be compared against words and descriptions within a particular domain. One standard algorithm may be to proceed to a search using the words that are part of a description, as well as synonyms or other words classified within or linked to that description. The resulting descriptions may be organized according to a heuristic or term ordering. Search results may include direct matches and approximate matches, the level of approximation equating to a display-worthy result being calculated by one or more different algorithms, examples of which may be generally known to those of skill in the art.

Additionally or alternatively, a search algorithm may make use of one or more terminology indices to determine whether an exact match to the user's query exists. In the event that the indices fail to yield a result, additional algorithms may be used to suggest possibilities to the user, e.g., "Do You Mean (DYM)"-type results. In addition, a search may yield a plurality of potential results, and result ranking heuristics may be used to address the particular field of use, e.g., one type of heuristic may be used to address medical informatics needs, while a second heuristic may be used in another field of use.

One or more terms may be returned to the user as a result of the search, and the user may be able to review the possible results to select the appropriate concept, e.g., the appropriate problem or procedure. The physician selects the appropriate term to capture the clinical intent, and the term(s) populates predetermined fields in the electronic record.

The selected term also contains mappings to one or more external codes, e.g., industry standard terminologies, such as ICD or SNO MED CT. Thus, the user's selection of the desired interface terminology automatically may provide necessary maps to those codes, allowing the physician to focus on patient care while at the same time capturing the necessary administrative and reference codes.

Implementation

Workflow may be straightforward. First, a host application may make a search request for terminology. Second, a response may be consumed by a service client, and the response may be in XML format. Third, the request may be fulfilled, and an XML response may be sent back to the service client.

Implementing this workflow may be accomplished using various languages. For example, the XML output implementation may occur via coding in a C, dot.Net C#, Java, Javascript, COBOL, PHP, or MUMPS environment.

By storing the interface terminology code in a patient's record, an EHR may be able to retrieve the most up-to-date administrative, clinical, and reference codes in the future. With interface terminology in place within an EHR, physicians find a number of beneficial impacts to their clinical workflow, including:

Improved diagnostic search results for physicians to locate problems;

More clinically meaningful physician documentation;

Creation of better and more complete problem lists; and

Improved coding accuracy and reliability.

Importance of Interface Terminology

Interface terminology provides a stable and constant pivot point to meet the changing coding requirements of the healthcare industry. Depending upon the EHR functionality, organizations can extract the terms and associated codes for analysis.

Interface terminology in the EHR may provide several benefits to health information management (HIM) professionals. Knowing how the terminology works in the EHR may help to ensure that an organization is reaping all the benefits of the system. The interface terminology may affect how information is managed, from impacting the revenue cycle to the design of the physician's search experience and preservation of the clinical intent within the longitudinal EHR.

Figure 6:
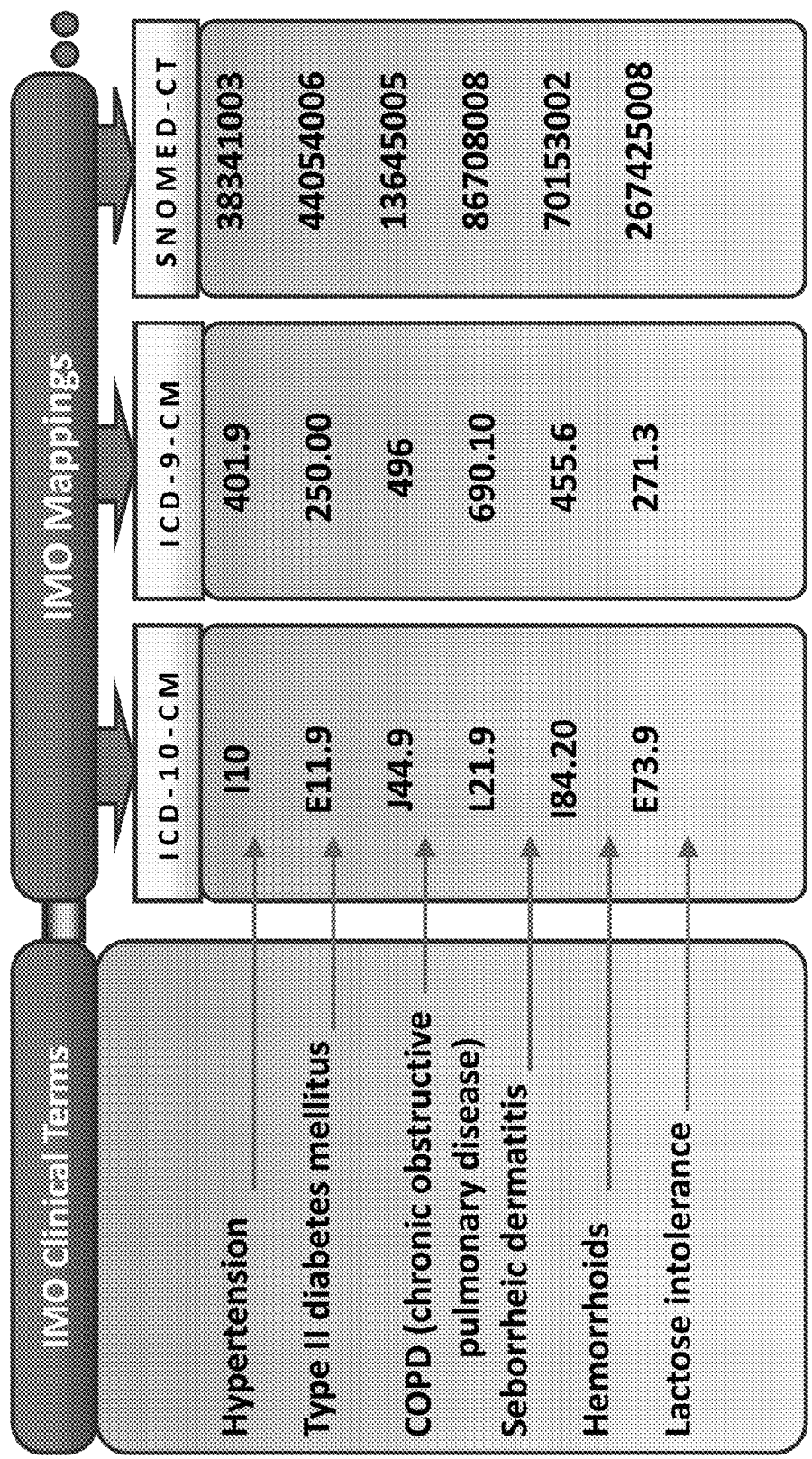
FIG. 6 is an example of a plurality of interface terminology concepts mapping to one or more respective external codes.

One goal of interface terminology may be to facilitate clinical documentation while streamlining other administrative functions of healthcare. Clinician-friendly terms with associated industry standard terminologies facilitate this goal. Interface terminology also may support a "capture once, use many times" philosophy of electronic health information. For example, if the term "CHF (congestive heart failure)" is captured with an associated ICD-9-CM code (428.0) or ICD-10-CM code (I50.9) and SNOMED CT code (42343007), the ICD code is routed to the financial system for review and claims generation, while the SNOMED CT code is available for other reporting. FIG. 6 illustrates how other descriptions (through their respective concepts) may be mapped to one or more external coding systems.

Clinical interface terminology may be used across multiple domains, e.g., problems, procedures (surgical, lab, imaging, medical), etc. By implementing interface terminology at the point of documentation, clinicians may be able to more easily focus on patient care while being able to capture clinical intent (e.g., capturing "left knee pain," even though the most appropriate external code may correspond to "knee pain" in SNOMED CT and "pain in joint, lower leg" in ICD-9). They also may be able to provide—indirectly—more accurate external codes for billing, decision support, and reporting, i.e., the system may provide for meaningful use.

Interface terminologies are important for problem lists. In practice, clinicians use many different synonyms, acronyms, eponyms, abbreviations, and other terms to describe the same diseases and problems. In terms of an interface terminology, each of these alternative terms may be a description under a common concept.

These alternate forms may be more familiar and frequently used in the clinical domain rather than ICD-9-CM, ICD-10-CM terms, or other external codes. Interface terminology provides an interface to the standard ICD-9-CM (or other code)-driven terminology in the EHR search. If the diagnosis was in standard ICD language, billing or other administrative tasks may be easier, but the clinician might have to alter the description or, depending upon the term, might even be unable to initially locate the diagnosis for selection. Additionally, the clinician then might have to work with an incomplete ICD description. Similarly, while billing or other administrative tasks may be simplified, the EHR may face significant issues capturing the visit diagnosis.

Instead, in this system and method, the physician selects an interface terminology diagnosis. The selected diagnosis populates the patient's problem list and other parts of the EHR. The selected interface terminology concept may be mapped to a preferred billable administrative code by administrative code sets, and that code may be used to populate the organization's billing system for review and claims generation to increase efficiency and accuracy in the revenue cycle.

Similarly, the selected interface terminology concept may map to one or more clinical and/or reference terminology terms. This mapping may allow the clinician or another user to research and retrieve information on all patients whose records include a reference to the concept.

In another example, once a problem has been diagnosed and/or coded, the user may order or engage in a course of treatment. This process may add additional complexity, in terms of both workflow and the implication of sub-domains. For example, the user may be a physician who orders a test, such as a "PSA Ultra." An "Ultrasensitive Prostate Antigen (PSA) Measurement" test, i.e., a performable procedure, may be performed. The user may select this test, which may have mappings to one or more administrative, clinical, and reference codes, which may result in a specific procedure (here, e.g., "CPT Code 84152 Prostate Specific Antigen (PSA); complexed (direct measurement)" being chargeable and billed. Resultables, which preferably correlate with the orderable, may be sent back from the lab and the results may be recorded in the EHR.

Each of these elements, i.e., the orderable, performable, resultable, and chargeable, may be recorded as data elements and/or data objects spanning one or more visits, within the patient's electronic medical record. Additionally, once completed, the procedure may be added to a list of historical procedures. One process of capturing and generating historical linkages for these data elements may be described in the commonly-assigned U.S. patent application Ser. No. 11/858,241, titled "Longitudinal Electronic Record and System." Additionally, the data elements may be coded with the appropriate interface terminology codes, which then may be linked to the appropriate external codes as described herein.

This method and system may have several benefits, e.g., it may:

Use familiar medical terms, which may reduce search time and increase precision;

Improve charge capture as a result of accurate diagnostic codes, resulting in quicker and more accurate billing;

Minimize maintenance, which may save the expense of creating and maintaining a term dictionary and complicated term-to-code mappings;

Provide meaningful use compliance;

Enable accurate data capture at the point of care; and

Increase patient safety through clarity of diagnosis, problem, and procedure descriptions.

Interface Terminology and Patient-Centered Care

Patients are the heart of healthcare. Today there is a renewed focus on patients as the driving force behind their received care, as the industry is striving for a holistic, patient-centered approach to providing care. Recent government regulations, such as accountable care organizations (ACOs), support and reinforce this idea. The ACO is a new care delivery model focused on a provider team to coordinate and manage healthcare services for a defined patient population. This coordinated care team is the designed point of contact to ensure that all of the patient's healthcare needs are being addressed regardless of setting or specialty. Accurate information is critical to managing patient populations effectively. This drives the need for longitudinal data sharing, which has been a challenge for the healthcare industry.

Interface terminologies can play a large role in the ability to store and share data across provider settings. They have the ability to capture clinical intent and create historical data to be available for longitudinal records. The needed level of clinical granularity is captured, which is important for continuity of care between providers. Having all associated maps for the terms also allows providers to know and manage their patient population. This robust data enables sound business practices for providers in addition to making the best decisions for their patients.

Interface terminology is vital to healthcare today and tomorrow as terminology is the foundation of documentation. The role of documentation does not change as records progress from paper to electronic format, i.e., the saying "if it is not documented, it was not done" still applies. But how the documentation is accomplished does change in the electronic environment, and efficiencies are gained by using an interface terminology.

Maintenance

Maintaining up to date and accurate information may be just as vital as the implementation and design of the EHR. As industry standard terminologies are updated, organizations engage in a maintenance process. Interface terminology eases the maintenance process for organizations.

For example, what happens if a diagnosis appears in a medical record, but the ICD code for that diagnosis is replaced? Interface terminology remains indefinitely in effect while the associated ICD code is updated to reflect the new code, i.e., the map to a code may change, while the record remains unchanged. This may be accomplished by redirecting the administrative code set maps. Alternatively, the original flag may remain pointed to the old code, and a new flag may be created to point between the interface terminology concept and the new code, e.g., in the case of secondary or less used codes and lexicals. In either event, the historical tags between the term and the prior ICD code may stay intact for historical purposes.

This updating may occur within an implementation workflow. For example, on day/visit one, the patient may present with "knee pain." The doctor may propose a treatment regimen, and the visit may be billed according to the "knee pain" ICD-9 external code, after which the visit may be closed. Later, a new ICD-9 external code may be assigned to "knee pain," by the Center for Medicare Services. This new external code then is mapped to that concept. Upon reopening the medical record for that patient and re-exploring that "knee pain" problem, the system will recognize that the concept of "knee pain" is mapped to a different ICD-9 external code, e.g., and will create a new revision of that problem with the updated external code map.

This process may eliminate physicians selecting diagnoses linked to out-of-date, incorrect, or non-billable codes, which in turn may help reduce the amount of needless communication and time spent between billing departments and clinicians to determine clinical intent and adjudicate coding discrepancies.

Deployment

The concept architecture for creation and maintenance of terminology described above preferably exists in a back-end environment. Conversely, the system may deploy a description- or lexical-based view on the data in the front end. This view may be more useful to the end users, as descriptions or lexical may more accurately reflect clinical intent and may comprise the terms most frequently used by the end users.

This front end deployment may include compiling and transmitting a lexical file, e.g., a text file, of all descriptions with flags indicating how the description might be used in the user interface. FIG. 4 may represent how the data for one domain—here, the problem domain—is presented to and is consumable by end users. Transformation processes take data from the tables of FIG. 3 to create FIG. 4 types of information. There are other domains that may be produced from FIG. 3, which may resemble FIG. 4, but for other domains, e.g., medications, procedures, etc.

This transformation may be aided by generating a table linking to and drawing from elements of both the table linking the concepts to the descriptions, e.g., the "Concept Description Map" table 128 and the external vocabulary table 162. This table may be considered the description-external vocabulary mapping table 170 and may include a column 170a listing codes between the multiple concepts and descriptions. This table also may include one or more columns 170b, 170c listing the external vocabulary codes or external codes. These columns may be generated specifically for this table, but preferably entries in the concept description map code column 170a may be derived from the concept description map code column 128a in the concept description map table 128. Similarly, entries in the external vocabulary code column 170b and external code columns 170c may be derived from the external vocabulary code column 162a and external code column 162b in external vocabulary table 162. (The external code column may include an entry indicating the code set, e.g., SNOMED CT, ICD-9, etc., from which the code values in the external vocabulary code column come.)

Deployment from FIG. 3 to FIG. 4 may occur in various ways, e.g., running a series of SQL statements to obtain and arrange the required information in the desired format. This information may be obtained by referencing the description-external vocabulary mapping table, and populating the deployment file with a plurality of entries, where each entry links a description with an external vocabulary identifier.

The lexical file that is deployed may include mappings between descriptions and the external codes to which they relate, which may support billing, reporting, or decision support workflows. While the actual mapping may occur at the concept level, the file presented to the user may not include mappings to interface terminology concepts, so the end users may not be aware of the number of concepts or the exact details of those concepts. With these mappings in place, the process of determining the external concepts to apply may become tantamount to a table lookup.

The deployment file may be available in multiple formats, including, but not limited to: comma-separated-value (CSV) ASCII format, tab-delimited ASCII format, database export formats, or other binary flat file formats. Described another way, the deployment file may be a distributable, computerized relational data source file. This deployment method also may rely upon a stateless, in-memory, software as a service (SAAS), for cloud deployment.

Deployment may occur in one or more fashions, e.g., via flat files in a relational database format or as part of a portal or web service.

The deployment method also may provide one or more of the following benefits:

Providing users with extensive alternative word choices and natural clinical language grammar, increasing the chance that the most accurate or most desirable concept is selected;

Presenting the user with one or more options that may reflect the user's clinical intent;

Presenting users with several linguistic versions such as synonyms, acronyms, abbreviations and alternate lexical variants;

Enabling enhanced granularity, e.g., adding specific disease and syndrome coding rather than broad, non-specific terms such as "other" or "unspecified;" and Insulating the user from translations between coding, clinical, and patient terminology, providing the user with an easier-to-use environment.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

What is claimed is:

1. A method for implementing an interface terminology in a longitudinal electronic medical record, the interface terminology comprising concepts and descriptions, a description being an alternative way to express a concept, the method comprising:

storing a plurality of concepts in a first table a database;

storing a plurality of descriptions in a second table in the database;

storing in a third table in the database linking information that links each description in the second table to a respective concept in the first table;

storing an external code set in a fourth table in the database, the external code set comprising a plurality of external codes; and mapping an external code to a respective concept via a directed graph structure linking each external code in the fourth table to the respective concept in the first table;

wherein said plurality of concepts provide a unique terminology for a user and can be added, updated, deleted, and merged;

wherein multiple of said plurality of descriptions may link to one of said plurality of concepts;

wherein said plurality of descriptions include terms used by both clinicians and patients;

wherein, for each concept, one of said plurality of descriptions is a preferred description for the linked concept and one of said plurality of descriptions is a preferred consumer term for the linked concept;

wherein multiple of said plurality of external codes may map to one of said plurality of concepts;

wherein said method for implementing an interface terminology serves the ends of capturing clinician's intent, driving financial aspects including billing, and driving analytical functions;

creating a longitudinal electronic medical record by:
  generating a first instance of a plurality of data objects during a first encounter, said plurality of data objects comprising data elements further comprising a first instance identifier and temporal identifiers;
  linking a data object in said first instance to a summarization reference with a pointer, where the plurality of data objects and the summarization reference are related as part of a directed graph data structure;
  creating an additional instance of a plurality of data objects during a later encounter, said additional instance of a plurality of data objects comprising data elements further comprising an additional instance identifier and temporal identifier; and
  providing continuity for said plurality of data objects of said first instance over time by tracking a relationship between said data object of said first instance and a data object of said additional instance;

tagging elements within a domain within the longitudinal electronic medical record with one or more of said plurality of descriptions; and displaying the preferred descriptions and the preferred consumer term.

2. The method according to claim 1, wherein the external code set is an administrative terminology.

3. The method according to claim 1, wherein the external code set is a clinical terminology.

4. The method according to claim 1, wherein the external code set is a reference terminology.

5. The method according to claim 1, further comprising: assigning a unique numerical identifier to each concept.

6. The method according to claim 1, wherein the mapping step includes indicating a type of relationship between the external code and the concept.

7. The method according to claim 6, wherein the relationship is one of:
same-as, broader-than, or narrower-than.

8. The method according to claim 1, wherein at least one concept includes a preferred clinician term and a preferred patient term linked as descriptions of that concept.

9. The method according to claim 1, the interface terminology comprising a plurality of domains, wherein each concept is unique within a domain.

10. The method according to claim 1, further comprising: abstracting similar descriptions for two concepts, such that the descriptions are different.

11. The method according to claim 1, further comprising: deploying a front-end file of the result of the mapping step, the front-end file comprising a link between the descriptions and the external code set.

12. The method according to claim 11, wherein the front-end file has a comma-separated-value ASCII format, a tab-delimited ASCII format, a database export format, or a binary flat file format.

13. The method according to claim 11, wherein the deploying step involves a cloud deployment that relies upon a stateless, in-memory database.

14. The method according to claim 1, further comprising: storing patient data in an electronic health record using the interface terminology.

15. A method for implementing an interface terminology in a longitudinal electronic medical record in at least one database, the interface terminology including a plurality of concepts and a plurality of descriptions, a description being an alternative way to express a concept, comprising:
  generating a concept table including a column storing a plurality of concept identifiers;
  generating a description table including a column storing a plurality of description identifiers;
  linking the concept table to the description table via a directed graph structure;
  generating an external vocabulary table including a column storing a plurality of external vocabulary identifiers; and linking the concept table to the external vocabulary table via a directed graph structure;

wherein said plurality of concept identifiers provide a unique terminology for a user and can be added, updated, deleted, and merged;

wherein multiple entries in said description table may link to one entry of said concept table;

wherein said plurality of description identifiers include terms used by both clinicians and patients;

wherein, for each concept, one of said plurality of descriptions is a preferred description for the linked concept and one of said plurality of descriptions is a preferred consumer term for the linked concept;

wherein said method for implementing an interface terminology serves the ends of capturing clinician's intent, driving financial aspects including billing, and driving analytical functions;

creating a longitudinal electronic medical record by:
  generating a first instance of a plurality of data objects during a first encounter, said plurality of data objects comprising data elements further comprising a first instance identifier and temporal identifiers;
  linking a data object in said first instance to a summarization reference with a pointer, where the plurality of data objects and the summarization reference are related as part of a directed graph data structure;
  creating an additional instance of a plurality of data objects during a later encounter, said additional instance of a plurality of data objects comprising data elements further comprising an additional instance identifier and temporal identifier; and
  providing continuity for said plurality of data objects of said first instance over time by tracking a relationship between said data object of said first instance and a data object of said additional instance;

tagging elements within a domain within the longitudinal electronic medical record with one or more of said plurality of descriptions; and displaying the preferred descriptions and the preferred consumer term.

16. The method according to claim 15, wherein the step of linking the concept table to the external vocabulary table comprises:

generating a mapping table;
linking the concept table to the mapping table; and
linking the external vocabulary table to the mapping table.

17. The method according to claim 16, wherein the mapping table includes mappings between multiple concepts in the concept table and one external vocabulary identifier in the external vocabulary table.

18. The method according to claim 16, wherein the mapping table includes mappings between one concept in the concept table and a plurality of external vocabulary identifiers in the external vocabulary table.

19. The method according to claim 15, wherein the step of linking the concept table to the description table comprises:
generating a mapping table;
linking the concept table to the mapping table; and
linking the description table to the mapping table.

20. The method according to claim 19, further comprising:
generating a description-external vocabulary mapping table;
linking the mapping table to the description-external vocabulary mapping table; and
linking the external vocabulary table to the description-external vocabulary mapping table.

21. The method according to claim 20, wherein the description-external vocabulary mapping table includes at least one column from the mapping table and at least one column from the external vocabulary table.

22. The method according to claim 20, further comprising:
generating a deployment file, the generating step comprising:
referencing the description-external vocabulary mapping table; and
populating the deployment file with a plurality of entries, wherein each entry links a description with an external vocabulary identifier.

23. A method for implementing an interface terminology in a longitudinal electronic medical record, the interface terminology comprising a plurality of concepts and a plurality of descriptions, a description being an alternative way to express a concept, the method comprising:
linking, in a database, each concept to two or more respective descriptions via a directed graph structure;
storing, in a database, an external code set comprising a plurality of external codes;
mapping each concept to a respective external code via a directed graph structure; and
deploying a front-end file, the front-end file comprises a link between the descriptions and the external code set;
wherein each said respective concept provides a unique terminology for a user and can be added, updated, deleted, and merged;
wherein said descriptions in said database include terms used by both clinicians and patients;
wherein, for each concept, one of said plurality of descriptions is a preferred description for the linked concept and one of said plurality of descriptions is a preferred consumer term for the linked concept;
wherein each said concept may map to more than one of said plurality of external codes; and
wherein said method for implementing an interface terminology serves the ends of capturing clinician's intent, driving financial aspects including billing, and driving analytical functions;
creating a longitudinal electronic medical record by:
generating a first instance of a plurality of data objects during a first encounter, said plurality of data objects comprising data elements further comprising a first instance identifier and temporal identifiers;
linking a data object in said first instance to a summarization reference with a pointer, where the plurality of data objects and the summarization reference are related as part of a directed graph data structure;
creating an additional instance of a plurality of data objects during a later encounter, said additional instance of a plurality of data objects comprising data elements further comprising an additional instance identifier and temporal identifier; and
providing continuity for said plurality of data objects of said first instance over time by tracking a relationship between said data object of said first instance and a data object of said additional instance;
tagging elements within a domain within the longitudinal electronic medical record with one or more of said plurality of descriptions; and
displaying the preferred descriptions and the preferred consumer term.

24. The method according to claim 23, further comprising:
adding a new description for one of the concepts;
linking the new description to the concept; and
re-deploying the front-end file, the front-end file comprises a link between the new description and a code in the external code set;
wherein the re-deploying step occurs without the need to re-map the concept to its respective external code.

25. The method according to claim 23, further comprising:
adding a new external code;
mapping at least one concept to the new external code; and
re-deploying the front-end file, the front-end file comprising a link between at least one description and the new external code;
wherein the mapping step occurs without the need to re-link the at least one description to the at least one concept.

26. The method according to claim 23, wherein each concept resides in a domain, and further wherein each external code in the external code set maps to concepts in one domain.

27. The method according to claim 23, wherein each concept resides in a domain, and further wherein each external code in the external code set maps to concepts in more than one domain.

28. The method according to claim 23, wherein each concept includes a description that is the same as that concept.

29. The method according to claim 23, wherein patient data is stored in an electronic health record using the interface terminology.

* * * * *